(12) United States Patent
Chen et al.

(10) Patent No.: US 9,675,789 B2
(45) Date of Patent: Jun. 13, 2017

(54) EMBEDDABLE MICRO-NEEDLE PATCH FOR TRANSDERMAL DRUG DELIVERY AND METHOD OF MANUFACTURING THE SAME

(75) Inventors: Mei-Chin Chen, Tainan (TW); Shih-Fang Huang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 204 days.

(21) Appl. No.: 13/610,203

(22) Filed: Sep. 11, 2012

(65) Prior Publication Data

US 2014/0005606 A1    Jan. 2, 2014

(30) Foreign Application Priority Data

Jun. 29, 2012 (TW) .............................. 101123681 A

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 9/5036* (2013.01);
(Continued)

(58) Field of Classification Search
CPC ...... A61M 2025/0093; A61M 37/0015; A61M 2037/0046; A61M 5/3295; A61M 5/3298;
(Continued)

(56) References Cited

U.S. PATENT DOCUMENTS 6,368,356 B1 *  4/2002  Zhong et al. .............. 623/23.75
7,364,875 B2 *  4/2008  Prescott et al. ............. 435/68.1
(Continued)

FOREIGN PATENT DOCUMENTS

EP         2338557 A1 *  6/2011
WO    WO 2008053481 A1 *  5/2008 ........ A61M 37/0015

OTHER PUBLICATIONS

Lim Soo, P., Cho, J., Grant, J., Ho, E., Piquette-Miller, M., & Allen, C. (2008). Drug release mechanism of paclitaxel from a chitosan-lipid implant system: Effect of swelling, degradation and morphology. European Journal of Pharmaceutics and Biopharmaceutics, 69(1), 149-157.*

(Continued)

*Primary Examiner* — Bhisma Mehta
*Assistant Examiner* — Nilay Shah
(74) *Attorney, Agent, or Firm* — Muncy, Geissler, Olds & Lowe, P.C.

(57) ABSTRACT

An embeddable micro-needle patch for transdermal drug delivery and method of manufacturing the same are disclosed. The embeddable micro-needle patch for transdermal drug delivery comprises a supporting substrate, on which the surface includes a plurality of extruded supporting shafts; a biodegradable carrier, which is formed of biodegradable polymer material and disposed on the supporting shaft; and drugs, which are encapsulated in the biodegradable carrier. When the embeddable micro-needle patch for transdermal drug delivery is attached to the skin for a predetermined time, the biodegradable carrier is separated from the supporting shafts and embedded into the skin, and the biodegradable carrier may swell and then degrade, so as to release the drugs, which are encapsulated in the biodegradable carrier, at a rate of 1%-99% loaded drug per day into the (Continued)

skin. Accordingly, velocity of releasing the drugs may be regulated, so as to sustain the drug efficacy.

**14 Claims, 10 Drawing Sheets
(2 of 10 Drawing Sheet(s) Filed in Color)**

(51) Int. Cl.
    *A61K 9/50*     (2006.01)
    *A61M 31/00*     (2006.01)
    *A61M 5/32*     (2006.01)

(52) U.S. Cl.
    CPC ......... *A61M 5/3295* (2013.01); *A61M 31/007* (2013.01); *A61M 2037/0046* (2013.01); *A61M 2037/0053* (2013.01)

(58) Field of Classification Search
    CPC .................. A61M 5/32; A61M 31/007; A61M 2037/0023; A61M 2037/0053
    USPC .................................................. 604/272–274
    See application file for complete search history.

(56) References Cited

U.S. PATENT DOCUMENTS

| | | | |
|---|---|---|---|
| 8,353,863 B2* | 1/2013 | Imran | 604/57 |
| 2003/0073979 A1* | 4/2003 | Naimark et al. | 604/891.1 |
| 2004/0106904 A1* | 6/2004 | Gonnelli | A61B 17/205 604/173 |
| 2008/0269685 A1* | 10/2008 | Singh et al. | 604/173 |
| 2010/0204678 A1* | 8/2010 | Imran | A61M 37/0069 604/511 |
| 2011/0152792 A1* | 6/2011 | Takada | 604/272 |

OTHER PUBLICATIONS

Chu, L. Y., & Prausnitz, M. R. (2011). Separable arrowhead microneedles. Journal of Controlled Release, 149(3), 242-249.*

* cited by examiner

EMBEDDABLE MICRO-NEEDLE PATCH FOR TRANSDERMAL DRUG DELIVERY AND METHOD OF MANUFACTURING THE SAME

CROSS-REFERENCE TO RELATED APPLICATION

This application claims the benefit of Taiwan Patent Application No. 101123681, filed on Jun. 29, 2012, in the Taiwan Intellectual Property Office, the disclosure of which is incorporated herein by reference.

BACKGROUND OF THE INVENTION

1. Field of the Invention

The present invention generally relates to a patch for transdermal drug delivery and method of manufacturing the same, in particular to an embeddable micro-needle patch for transdermal drug delivery having biodegradable polymeric materials and method of manufacturing the same.

2. Description of the Related Art

In current drug therapy paths, oral administration and hypodermic injection are the most frequently seen methods, wherein oral administration is convenient and easily obtained to become the main manner of drug therapy. However, many oral medicines are firstly decomposed in gastrointestinal system and then enter into blood circulation systems to generate treatment effect by the first-pass metabolism effect of the liver. The treatment effect is unable to be precisely controlled since the foregoing progress is too long and may be influenced by the effect of digestive system. In addition, hypodermic injection is an invasive treatment. Patients may feel more painful during the injection, and the needle head and the wound may be infected to cause safety concerns.

The transdermal drug delivery system is a novel drug therapy path capable of overcoming the defect of the foregoing two manners of drug therapy. It does not only prevent the drug efficacy of oral medicines from losing due to the digestion of gastrointestinal system but also reduces pain and infection caused by hypodermic injection. However, the outermost layer of human skin is stratum corneum that is a very important protection barrier for human bodies and belonging to hydrophobicity and having negative charges. Consequently, macro-molecular drugs and hydrophilic drugs are difficult to penetrate through to cause the serious barrier in developing the transdermal drug delivery system.

To overcome the foregoing problem, a technique of combining a conventional needle treatment with the transdermal patch is recently developed. The technique is composed of a patch fully distributed with micro-needles. These micro-needles can directly penetrate through stratum corneum of skin to effectively deliver macro-molecular drugs and hydrophilic drugs, such as vaccines, proteins, insulin or DNA (deoxyribonucleic acid), that are difficult to pass through skin to epidermis of skin. These drugs then enter the body via blood circulation after absorbing by distal micro vascular, thereby achieving treatment effect.

However, the micro-needle patch sale in markets is usually made of metal materials or silicon materials. The user must take the infection risk probably caused by broken micro-needles or repeatedly using micro-needles. These micro-needle patches may also cause the danger of medical waste and need to be in touch with skin for long time to cause allergic reaction such as skin pruritus and red and swollen. In addition, the currently developed micro-needle patch usually belongs to the formula of rapidly releasing drugs. It does not have the prolonged action formula capable of continuously releasing the drugs. Therefore, improving micro-needle materials, structures, and usage manner, and controlling time of releasing the drugs from the patch for transdermal drug delivery are an important issue of researching and developing the patch for transdermal drug delivery system.

SUMMARY OF THE INVENTION

Therefore, it is a primary objective of the present invention to provide an embeddable micro-needle patch for transdermal drug delivery having biodegradable polymeric materials and its manufacturing method to achieve the efficacy of controlling the efficiency of releasing drugs after the biodegradable polymeric materials are swollen and then degraded in skin.

To achieve the foregoing objective, the present invention provides an embeddable micro-needle patch for transdermal drug delivery comprising a supporting substrate, on which its surface comprises a plurality of protruded supporting shafts; a biodegradable carrier formed by a biodegradable polymeric material and disposed on the supporting shafts; and a drug encapsulated in the biodegradable carrier. When the embeddable micro-needle patch for transdermal drug delivery is applied on skin for a predetermined time, the biodegradable carrier is embedded into skin by separating from the supporting shafts, and the biodegradable carrier is swollen and then degraded in skin to release the drug encapsulated in the biodegradable carrier into skin at a rate of 1% loaded drug per day to 99% loaded drug per day.

The predetermined time of applying the embeddable micro-needle patch for transdermal drug delivery according to the present invention on skin is 0.1 second to one hour.

Preferably, the material of the supporting substrate of the embeddable micro-needle patch for transdermal drug delivery according to the present invention can include polylactic acid (PLA), polyglycolic acid (PGA), poly-lactide-co-glycolide (PLGA) and polydioxanone (PDS) or derivative thereof.

In addition, the supporting shafts on the supporting substrate can be adhered to the biodegradable carrier by coating an adhesive layer. The material of the adhesive layer can include polyethylene glycol (PEG), polyethylene oxide (PEO), polyvinylpyrrolidone (PVP), polyvinyl alcohol (PVA), gamma-polyglutamic acid (γ-PGA), gelatin, maltose, xanthan gum and various water-soluble carbohydrate and derivatives thereof.

Preferably, the shape of the biodegradable carrier of the embeddable micro-needle patch for transdermal drug delivery according to the present invention can include a micro-needle, a pyramid, a cone or any shape capable of enabling the biodegradable carrier penetrating though skin. The depth for the biodegradable carrier penetrating through skin can be 20 μm to 1000 μm. Preferably, the material of the biodegradable carrier of the embeddable micro-needle patch for transdermal drug delivery according to the present invention can include chitosan, chitin, silk, carboxymethyl cellulose (CMC), chondroitin, collagen, gelatin, the foregoing cross-linked material, the foregoing derivatives, or polysaccharide derivative.

Preferably, the drug encapsulated in the embeddable micro-needle patch for transdermal drug delivery according to the present invention can include hydrophilic drugs or macromolecular drugs having a molecular weight greater than 500 Da, such as DNA (deoxyribonucleic acid), protein, vaccine, peptide, bacteria or chemical synthetic drug.

In addition, the present invention further provides a method for manufacturing an embeddable micro-needle patch for transdermal drug delivery. The method comprises the following steps of: mold-filling a biodegradable polymer gel containing a drug to obtain a plurality of biodegradable carriers; and adhering a plurality of protruded supporting shafts on a surface of a supporting substrate to the plurality of biodegradable carriers to form the embeddable micro-needle patch for transdermal drug delivery.

The step of mold-filling the biodegradable polymer gel containing the drug further comprises placing the biodegradable polymer gel containing the drug on a surface of a mold to perform centrifugation at 4500 rpm (3350×g) to 5000 rpm (3880×g) such that the biodegradable polymer gel containing the drug is injected into cavities of the mold.

Preferably, the step of mold-filling the biodegradable polymer gel containing the drug further comprises performing the biodegradable polymer gel containing the drug, which is injected into the cavities of the mold, with a centrifugal force again at 4500 rpm (3350×g) to 5000 rpm (3880×g) such that the biodegradable polymer gel containing the drug is concentrated at bottoms of the cavities contained by the mold.

Preferably, the step of mold-filling the biodegradable polymer gel containing the drug further comprises concentrating the biodegradable polymer gel containing the drug, which is injected into the cavities of the mold, at bottoms of the cavities contained by the mold through a pressing tool.

The cavities of the mold for use in mold-filing are a micro-needle column, a pyramid column or a cone column shape.

The embeddable micro-needle patch for transdermal drug delivery according to the present invention has one or more advantages:

1. The current developed polymer micro-needle patch belongs to a fast drug releasing formulation. It does not have long-term formulation capable of continuously releasing drugs. The carrier of the transdermal patch according to the present invention is formed by the biodegradable polymer material. The speed of drug release depends on the swelling and degradation of the carrier. Sustained drug release and prolonged drug efficacy can be achieved by adjusting the rates of these two factors.

2. The transdermal patch according to the present invention is that the carrier is embedded into skin by separating from the supporting substrate. Its operation is simple and does not need to adhere the transdermal patch to skin long term. By comparing with medicine sale in markets, it prevents the user from being uncomfortable.

3. The transdermal patch according to the present invention is formed by using the biodegradable polymer material and does not have the problem of treating medical waste.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed structure, operating principle and effects of the present invention will now be described in more details hereinafter with reference to the accompanying drawings that show various embodiments of the invention as follows.

DETAILED DESCRIPTION OF THE PREFERRED EMBODIMENTS

The technical content of the present invention will become apparent by the detailed description of the following embodiments and the illustration of related drawings as follows.

"Transdermal" is taken as a professional terminology and is that a chemical agent (i.e. therapeutic agents or immunological active agents of drugs, vaccines and the like) is delivered to partial tissues or body circulatory system without physical skin cutting (e.g. surgical knives). Generally, "transdermal" is a non-invasive or micro-invasive drug delivery.

Figure 1:
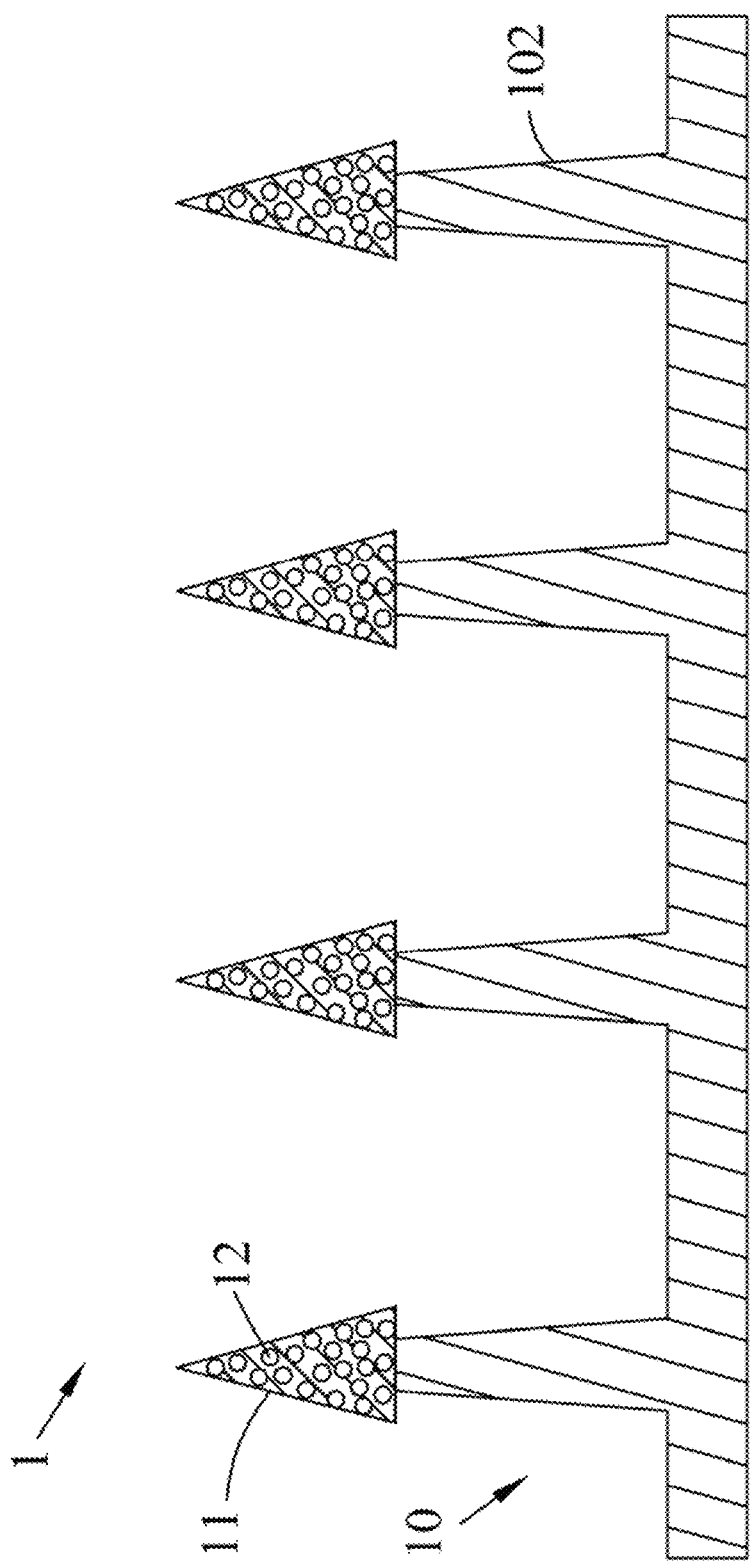
FIG. 1 is a schematic diagram of an embeddable micro-needle patch for transdermal drug delivery according to an embodiment of the present invention.

With reference to FIG. 1 for a schematic diagram of an embeddable micro-needle patch for transdermal drug delivery according to an embodiment of the present invention is depicted. In FIG. 1, the embeddable micro-needle patch for transdermal drug delivery 1 contains a supporting substrate 10, wherein its surface comprises a plurality of extruding supporting shafts 102; a biodegradable carrier 11 formed by a biodegradable polymeric material and disposed on the plurality of supporting shafts 102; and drugs 12 encapsulated in the biodegradable carrier 11.

In the embodiment, the supporting substrate 10 can be formed by materials of biodegradable polyester polymer and copolymer having higher mechanical strength, such as poly-lactic acid (PLA), polyglycolic acid (PGA), poly-lactide-co-glycolide (PLGA) and polydioxanone (PDS) or derivative thereof.

To allow the biodegradable carrier 11 penetrating through skin, the biodegradable carrier 11 can, but not limited to, include a micro-needle, a pyramid, a cone or any shape capable of enabling the carrier penetrating though skin. Moreover, the greatest difference between the transdermal patch and a conventional injection is that the former is a micro-invasive medical treatment. The height and the width of the carrier 11 of the invention should not too high or too wide to prevent the carrier 11 from penetrating too deep, thereby harming or injuring a user. Therefore, the height of the biodegradable carrier 11 is preferably about 400 μm to 800 μm. The base width of the biodegradable carrier 11 is preferably 200 μm to 400 μm. The height of the supporting shafts 102 is preferably about 600 μm to 900 μm. The base width of the supporting shafts 102 is preferably 200 μm to 400 μm. With the foregoing features, the biodegradable carrier 11 can penetrate through the cuticle of skin to reach epidermis. Preferably, its penetration depth can be about 250 μm to 800 μm.

The supporting shafts 102 of the supporting substrate 10 are bound to the biodegradable carrier 11 through an adhesive. When the biodegradable carrier 11 disposed on the supporting shafts 102 penetrate through the skin, the biodegradable carrier 11 can be easily separated with the supporting shafts 102 to embed into the skin. The adhesive coated on the supporting shafts 102 can include, but not limited to, polyethylene glycol (PEG), polyethylene oxide (PEO), polyvinylpyrrolidone (PVP), polyvinyl alcohol (PVA), gamma-polyglutamic acid (γ-PGA), gelatin, maltose, xanthan gum and various water-soluble carbohydrate and derivatives thereof.

In the embodiment of the present invention, the biodegradable carrier 11 can be, but not limited to, composed of biodegradable polymeric materials such as chitosan, chitin, silk, carboxymethyl cellulose (CMC), chondroitin, collagen, gelatin, the foregoing crosslinked material, the foregoing derivatives, or polysaccharide derivative. When the biodegradable carrier 11 is separated from the supporting shaft 102 to embed into skin, it can be swelled and then naturally degrade such that medicine 12 encapsulated therein can be released into skin.

In the embodiment, the time for the drugs 12 released into skin can be decided according to the molecular weight of the polymeric material formed into the biodegradable carrier 11 and the drugs 12. If the molecular weight of the material used in the biodegradable carrier 11 is great, its molecular chain is easily wound with the drugs 12 to achieve the sustained release effect. It should be noted that "sustained release" described in the specification is taken as the terminology, and the terminology is that the reagent (e.g. therapeutic agents of drugs, vaccines or immunological active agents) is stably released within a certain time in an approximately fixed concentration and not violently increased in the short run.

Therefore, the transdermal patch disclosed by the present invention can control the speed of releasing the drugs 12 by regulating the material of forming the biodegradable carrier 12 to ensure that the drugs 12 are continuously released within a certain unit time, thereby achieving the effect of retaining drug efficacy. The mechanism of sustained-releasing drugs through the embeddable micro-needle patch for transdermal drug delivery according to the present invention is subsequently described in detail.

The biodegradable carrier 11 of the embeddable micro-needle patch for transdermal drug delivery according to the present invention can penetrate through the cuticle to reach epidermis and be swelled and then naturally degrade to release the drugs 12 encapsulated therein. Therefore, the drugs 12 can include the hydrophilic drug or macromolecular drugs having the molecular weight is greater than 500 Da, which is difficult to penetrate through skin cuticle, such as DNA (deoxyribonucleic acid), macromolecular protein, vaccine, peptide, bacteria or chemical synthetic drug.

Moreover, in the embeddable micro-needle patch for transdermal drug delivery according to the present invention, its materials use biodegradable polymeric materials so that it can be naturally decomposed or absorbed and metabolized by human bodies. Thus, the biodegradable carrier 11 embedded into skin may not affect the normal metabolism of the user, and the separated supporting substrate 10 may not have the problem of treating medical wastes as well.

To further understand the present invention and allow the ordinary skill in the art to implement the present invention, the manufacturing method of embeddable micro-needle patch for transdermal drug delivery according to the invention is depicted as the following. The used materials and parameters, including concentrations, contents, reaction time and the like are not taken as the restriction, and its similarity and equivalent scope must be contained therein.

Figure 2:
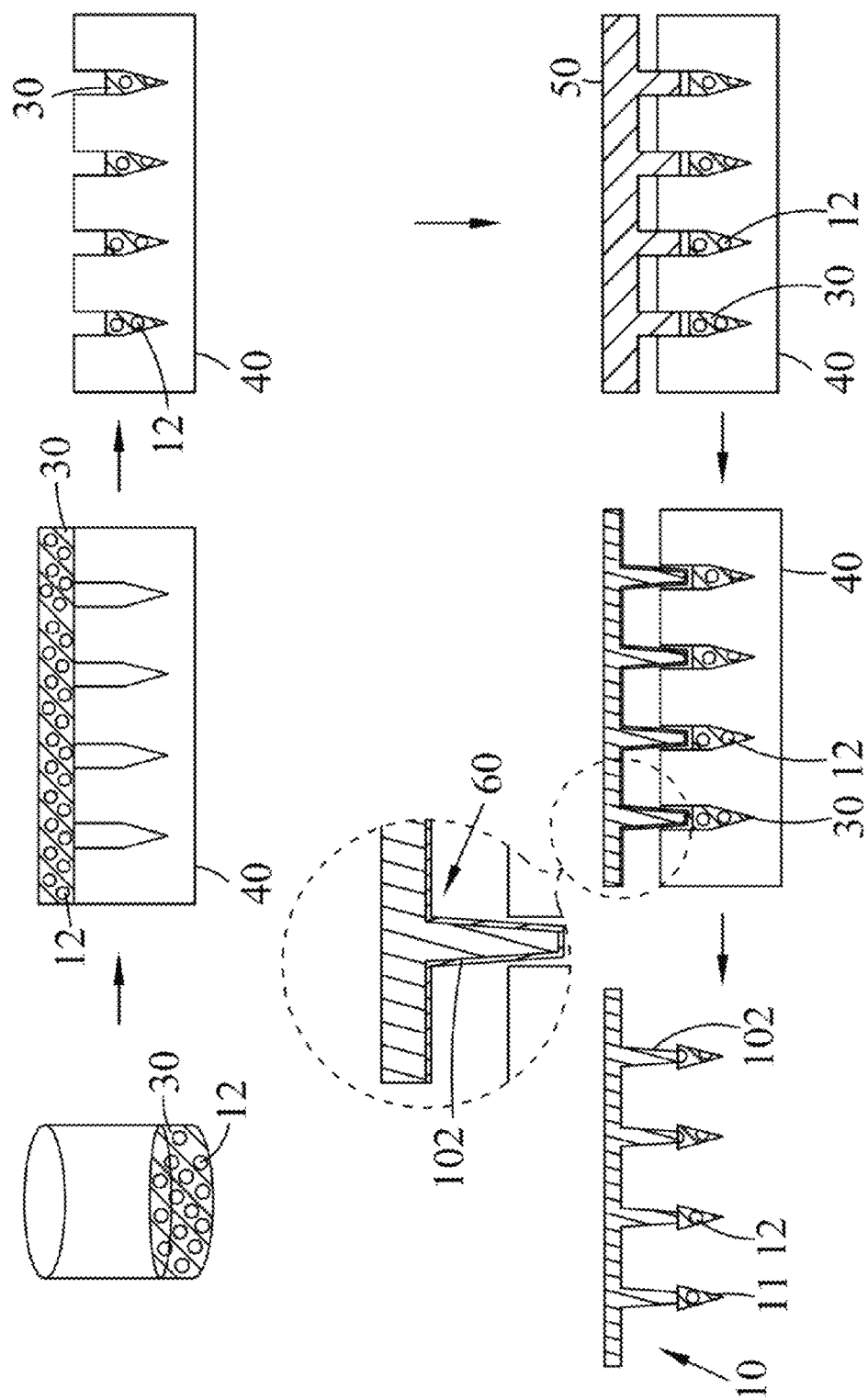
FIG. 2 is a schematic diagram of a method for manufacturing an embeddable micro-needle patch for transdermal drug delivery according to an embodiment of the present invention.

With reference to FIG. 2 for a schematic diagram of an embeddable micro-needle patch for transdermal drug delivery according to an embodiment of the present invention is depicted. Firstly, the biodegradable polymeric solution is added into 1% of acetic acid solution to uniformly mix the mixture, and the mixture then is placed in deionized water for dialysis till the pH value reaches pH~6. In the embodiment, chitosan solution is, but not limited to, taken as the biodegradable polymeric solution. The concentration of chitosan solution that has been dialyzed is about 1 wt %. 40 ml of 1 wt % of chitosan solution is added into 100 ml beaker and heated to reach 80° C. to evaporate additional water content until the concentration of chitosan solution is about 8 wt %. Afterward the drugs 12 to be encapsulated are added into the solution to uniformly stir the mixture. The added drugs can include the hydrophilic drugs or macromolecular drugs having a molecular weight greater than 500 Da, which are both difficult to penetrate through skin cuticle, such as DNA (deoxyribonucleic acid), macromolecular protein, vaccine, peptide, bacteria or chemical synthetic drug. The foregoing chitosan solution added with the drugs 12 is evaporated at 37° C. to form chitosan gel 30 (its concentration is about 10 wt %) containing the drugs.

100 mg of chitosan gel 30 containing the drugs is taken and placed on a mold 40. The mold 40 covered with the chitosan gel 30 having the drugs is placed in a centrifuge tube, the tube then is placed into a centrifuge machine, and centrifuges at 5000 rpm and room temperature condition for 2 hours. The cavity bottom of the mold is a micro-needle, a pyramid, a cone shape. To fill the chitosan gel 30 containing the drugs in the mold cavities, 150 mg of chitosan gel 30 containing the drugs is placed on the mold 40, and the mold is imposed with centrifugal force for 1 hour. The residual solution remained on the exterior and the surface of the mold cavities is removed at a microscope. At the same conditions, the mold then is imposed with centrifugal force for 30 minutes such that the chitosan gel 30 containing the drugs can enter the further bottom of the cavities of the mold 40 during the semi-dried state.

A pressing tool 50 then is used to push the chitosan gel 30 containing the drugs in the cavities of the mold 40 to concentrate it in cone cavity structures at the bottom of the mold 40. To tightly concentrate chitosan gel 30 containing the drugs in the cavities of the mold 40, 100 mg of chitosan gel 30 containing the drugs is placed on the mold 40, and the foregoing centrifugal step and the pressing step are repeated for 3 times. After performing semi-dried centrifugal force for 5 minutes, the supporting substrate 10 is accurately aligned and joined, wherein the supporting substrate 10 is firstly coated with the adhesive 60 to enhance the adhesion force between the support shafts 102 and the carrier 11. In the embodiment, 1 wt % of polyvinylpyrrolidone (PVP) is, but not limited to, taken as the adhesive agent. The semi-dried chitosan gel 30 containing the drugs is joined with the supporting shafts 102 and placed in a baking box at 37° C. After removing the mold, the embeddable micro-needle patch for transdermal drug delivery according to the invention can be obtained.

The method of embeddable micro-needle patch for transdermal drug delivery is, but not limited to, a depiction of preferable embodiment.

Figure 3:
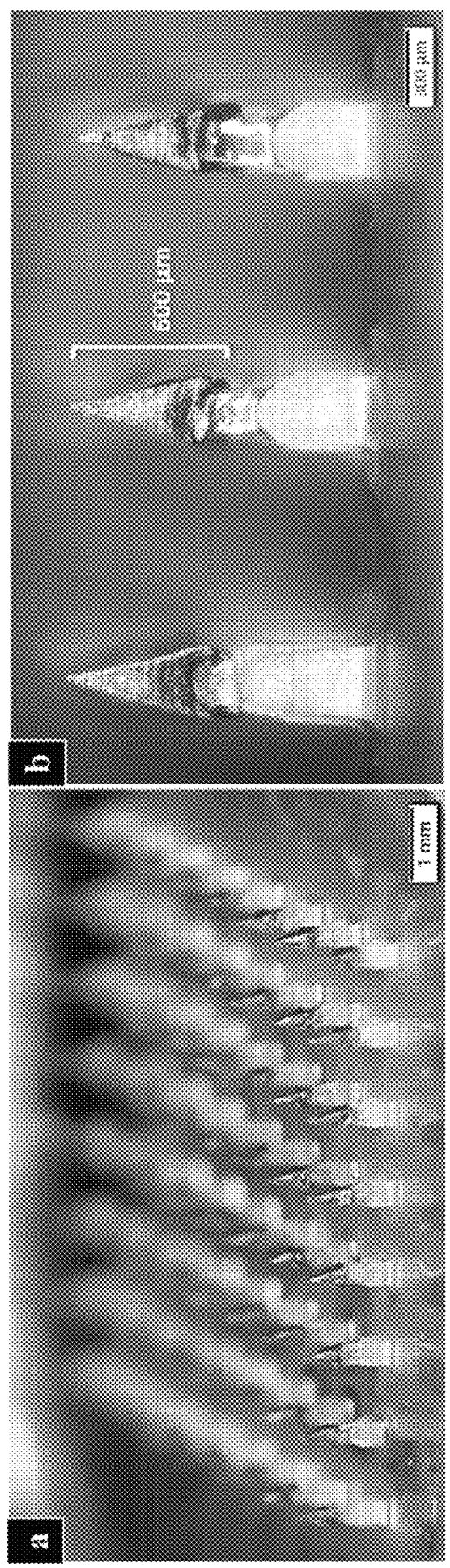
FIG. 3 is an image diagram of an embeddable micro-needle patch for transdermal drug delivery taken by a stereomicroscope in accordance with the present invention.

The embeddable micro-needle patch for transdermal drug delivery made of the foregoing method is shown in FIG. 3. FIG. 3 is an image diagram of an embeddable micro-needle patch for transdermal drug delivery taken by a stereomicroscope, wherein a part and b part in FIG. 3 are electron microscopy images that are respectively enlarged at single times and quadruple times. As shown in FIG. 3, the height of the carrier of the embeddable micro-needle patch for transdermal drug delivery is about 600 μm. The width of the base plate of the carrier is about 300 μm. The aspect ratio is about 2. The height of the supporting shaft is about 800 μm. The width of the base plate of the supporting shaft is about 300 μm.

It should be noted that the transdermal patch is to inject micro-needles into skin through an embedding mode. Therefore, the supporting shaft on the supporting substrate is mutually adhered to the carrier through the adhesive agent. Accordingly, the user can touch and press the supporting substrate without touching the carrier during the operation to avoid the pollution risk. Moreover, when the carrier penetrates through skin, the user can easily remove the supporting substrate to separate from the carrier due to the adhesion relationship between the carrier and the supporting shaft. Discomfort caused by sticking the transdermal patch for long time can be prevented. In addition, the supporting substrate of the transdermal patch according to the present invention can be made of biodegradable materials. The removed supporting substrate can be naturally decomposed or recycled to reuse after melting and sterilizing at high temperature. It can further prevent the resource from being wasted. In the subsequent paragraphs, the operation of the embeddable micro-needle patch for transdermal drug delivery according to the invention is depicted in detail.

Figure 4:
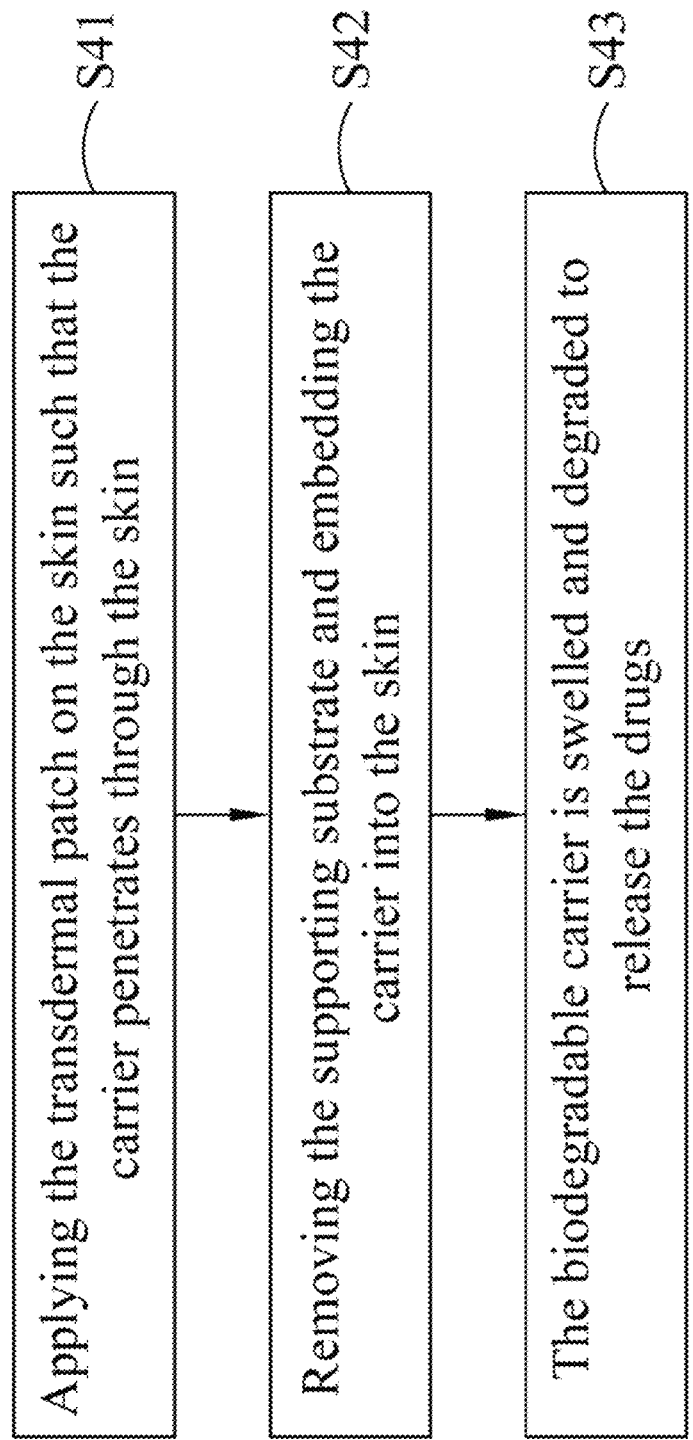
FIG. 4 is a flowchart of using an embeddable micro-needle patch for transdermal drug delivery according to the present invention.
Figure 5:
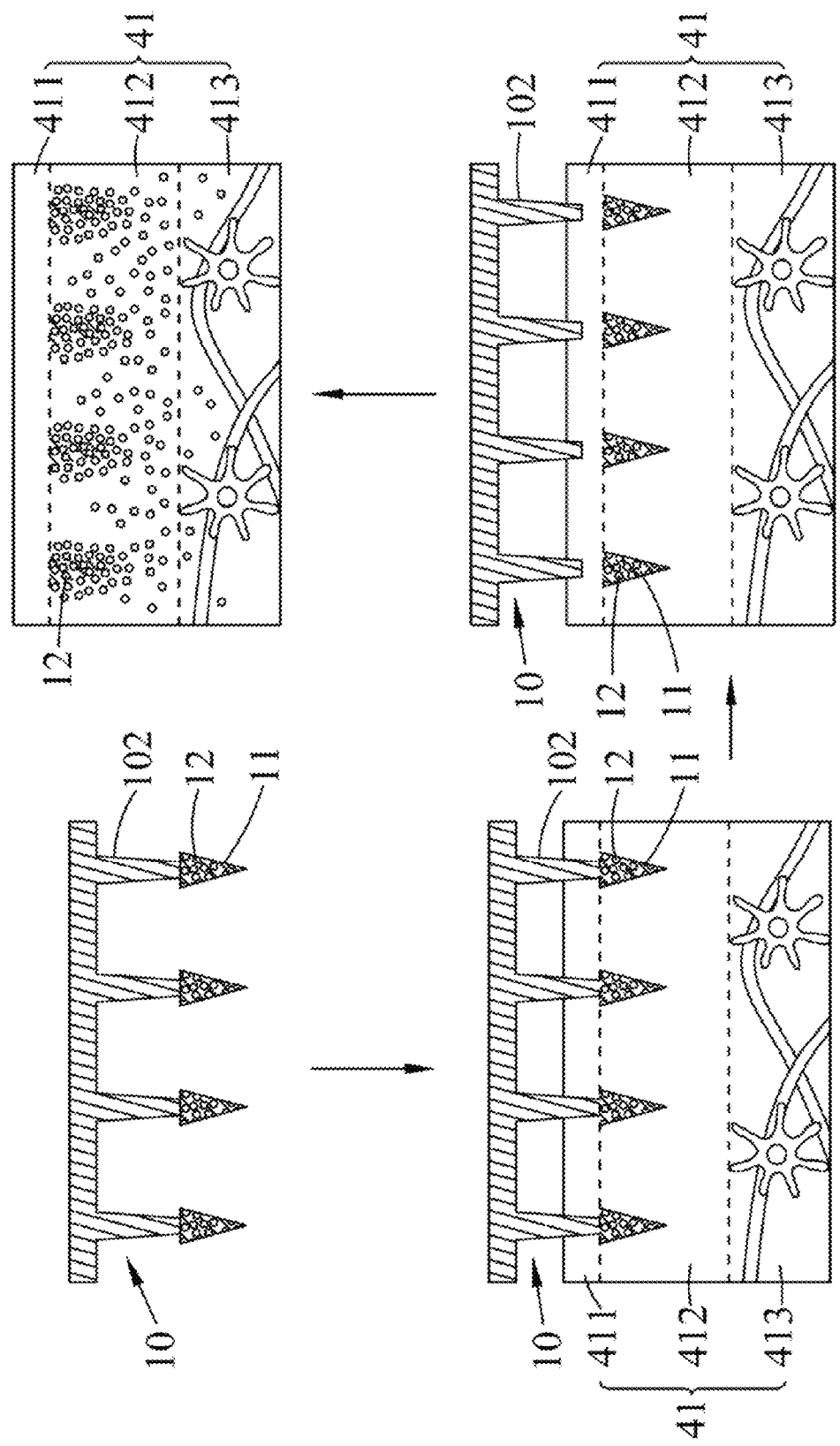
FIG. 5 is a schematic diagram of using an embeddable micro-needle patch for transdermal drug delivery according to the present invention.

With reference to FIG. 4 and FIG. 5, FIG. 4 is a flowchart of using the embeddable micro-needle patch for transdermal drug delivery according to the invention, and FIG. 5 is a schematic diagram of using the embeddable micro-needle patch for transdermal drug delivery according to the invention. With reference to FIG. 5, firstly, the transdermal patch is applied on skin for 3 to 30 minutes through a manner of manually pressing the supporting substrate 10 such that the carrier 11 on the supporting shaft 102 penetrates through skin 41 (step S41), wherein the carrier 11, as shown in FIG. 5, can penetrate through cuticles 411 of skin 41 to reach epidermis 412. It should be noted that the carrier 11 would not penetrate through dermis 413 having blood vessels and sensory nerves. Therefore, the user may not feel pain or bleed through the embeddable micro-needle patch for transdermal drug delivery according to the present invention. In addition, time of applying the embeddable micro-needle patch for transdermal drug delivery according to the present invention can be regulated according to different water retentions of users' skin. After the carrier 11 penetrates through skin 41, the supporting substrate 10 can be removed to embed the carrier 11 into skin 41 (step S42). Next, the biodegradable carrier 11 is swelled to release the drugs by contacting water content within skin. The swelled carrier 11 will be closely embedded in skin. Afterward the carrier 11 continuously releases the encapsulated drugs 12 in skin through natural degrading (step S43).

To demonstrate that the embeddable micro-needle patch for transdermal drug delivery according to the present invention could manually penetrate through skin and the front carriers are embedded into skin to release drugs, the experiment takes porcine cadaver skins as an example.

Figure 6:
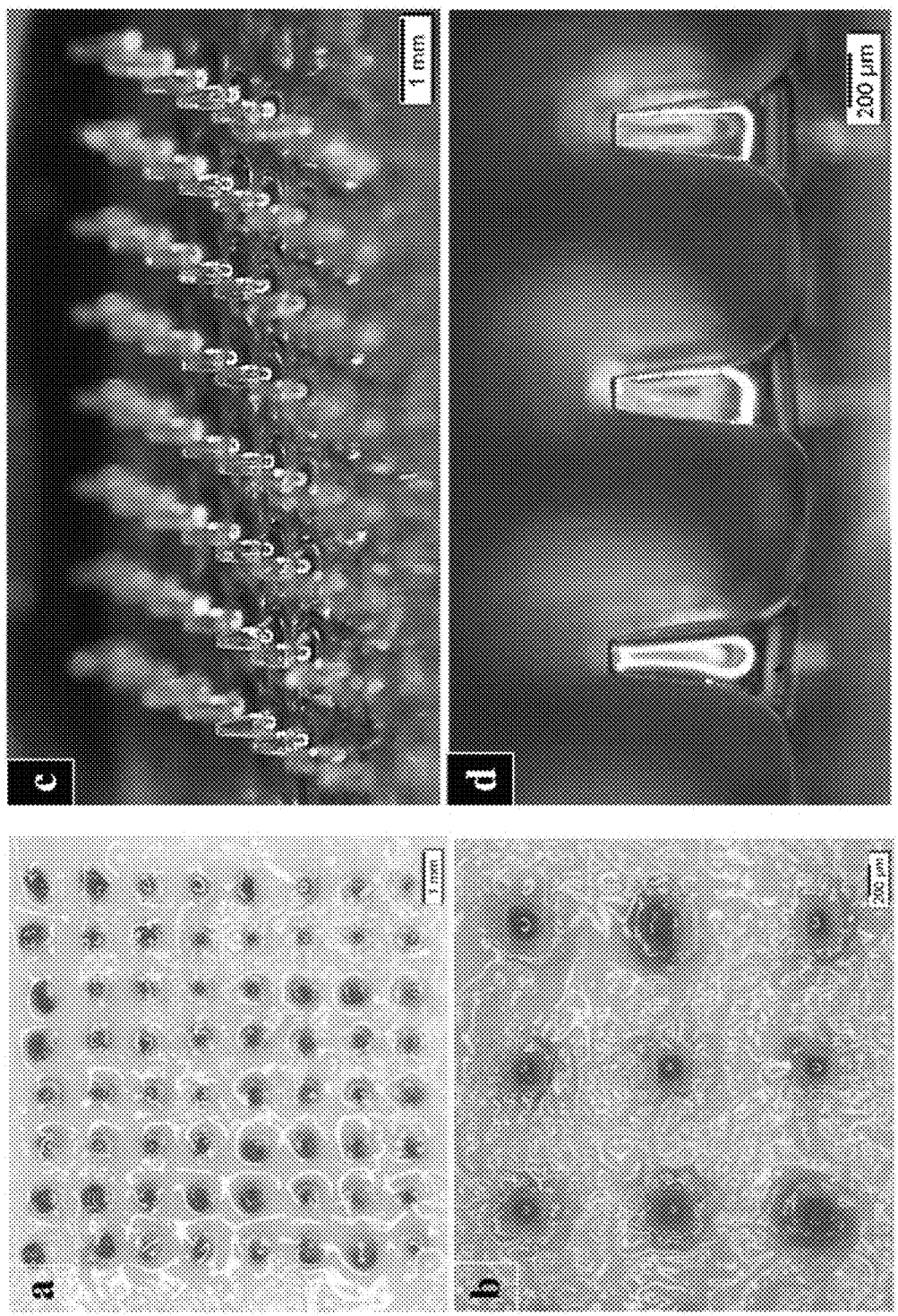
FIG. 6 is a testing result for an embeddable micro-needle patch for skin insertion penetrating through porcine cadaver skin according to the present invention; a part of FIG. 6 is the en face view of the micro-needle penetration sites on the porcine cadaver skin surface; b part of FIG. 6 is a magnification view of a part of FIG. 6; c part is the supporting substrate after skin insertion and separated from the Rhodamine 6G-labeled chitosan micro-needles; d part of FIG. 6 is a magnification view of c part of FIG. 6.

With reference to FIG. 6 for a testing result of allowing the embeddable micro-needle patch for transdermal drug delivery according to the present invention penetrating through porcine cadaver skins is provided. After the transdermal patch according to the present invention is applied on porcine cadaver skins for five minutes, the supporting substrate then is removed, wherein the carrier contains Rhodamine 6G to label chitosan. Its result is shown in a part of FIG. 6. a part of FIG. 6 is the en face view of the micro-needle penetration sites on the porcine cadaver skin surface. The porcine cadaver skin surface that has been penetrated by the transdermal patch for five minutes is exactly produced with gaps caused by the penetration of the carrier. A red dot array then is formed after the carrier containing red fluorescein dye penetrates through skin. b part of FIG. 6 is a magnification view of a part of FIG. 6. c part of FIG. 6 is the supporting substrate after skin insertion and separated from the Rhodamine 6G-labeled chitosan micro-needles. As shown in the figure, the supporting shafts on the removed supporting substrate do not label red fluorescein dye after penetrating for five minutes. In another word, there is no chitosan remain, representing that the carrier completely comes off the supporting shafts so as to embed into porcine cadaver skin.

Figure 7:
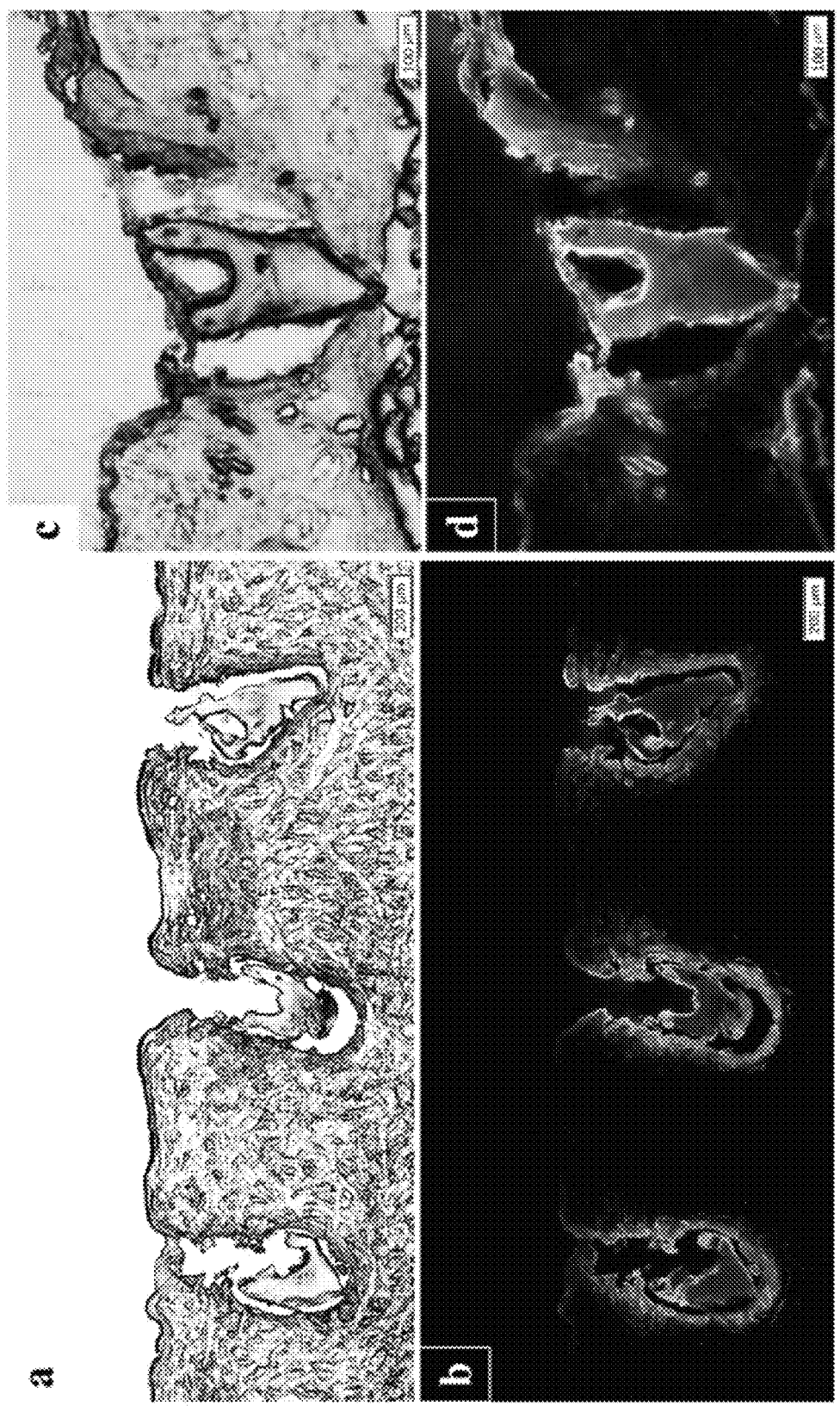
FIG. 7 is a testing result for an embeddable micro-needle patch for transdermal drug delivery penetrating through porcine cadaver skin and a mouse's skin according to the invention; a part and b part of FIG. 7 are a histological section after insertion a FITC-labeled chitosan micro-needles patch containing Rhodamine 6G-labeled drug into porcine cadaver skin; c part and d part of FIG. 7 are a histological section after insertion a FITC-labeled chitosan micro-needles patch containing Rhodamine 6G-labeled drug into mouse skin.

Further, in another aspect of the embodiment, the transdermal patch labeled by another fluorescence is used. It label chitosan through green fluorescence (FITC) and label the drugs to be released through red fluorescence (Rhodamine 6G). After the transdermal patch penetrates through a porcine cadaver skin and a live mouse's skin for five minutes, the supporting substrate is removed, and the porcine cadaver skin and the live mouse's skin then are prepared for histology. The section result is shown in FIG. 7. a part and c part of FIG. 7 are respectively a histological section after insertion a FITC-labeled chitosan micro-needles patch containing Rhodamine 6G-labeled drug into porcine cadaver skin and mouse skin by a visible light microscope. b part and d part of FIG. 7 are respectively a histological section after insertion a FITC-labeled chitosan micro-needles patch containing Rhodamine 6G-labeled drug into porcine cadaver skin and mouse skin by a fluorescent microscope. As shown in the figures, the carriers containing green fluorescent label is successfully embedded into the porcine cadaver skin and the skin tissue of the mouse. The encapsulated drugs containing red fluorescent label are initially released into tissues. The depth penetrated by the carriers is respectively about 500 μm and 300 μm.

With the foregoing experiment, the embeddable micro-needle patch for transdermal drug delivery according to the present invention can penetrate through skin by using hands, and the front carrier can be embedded into skin to achieve the effect of releasing the drugs. However, the drugs released by the embeddable micro-needle patch for transdermal drug delivery according to the present invention must have complete biological activity to bring the treatment effect into full play. Therefore, the subsequent paragraphs will further discuss in vitro and in vivo experiments of the embeddable micro-needle patch for transdermal drug delivery according to the present invention.

Figure 8:
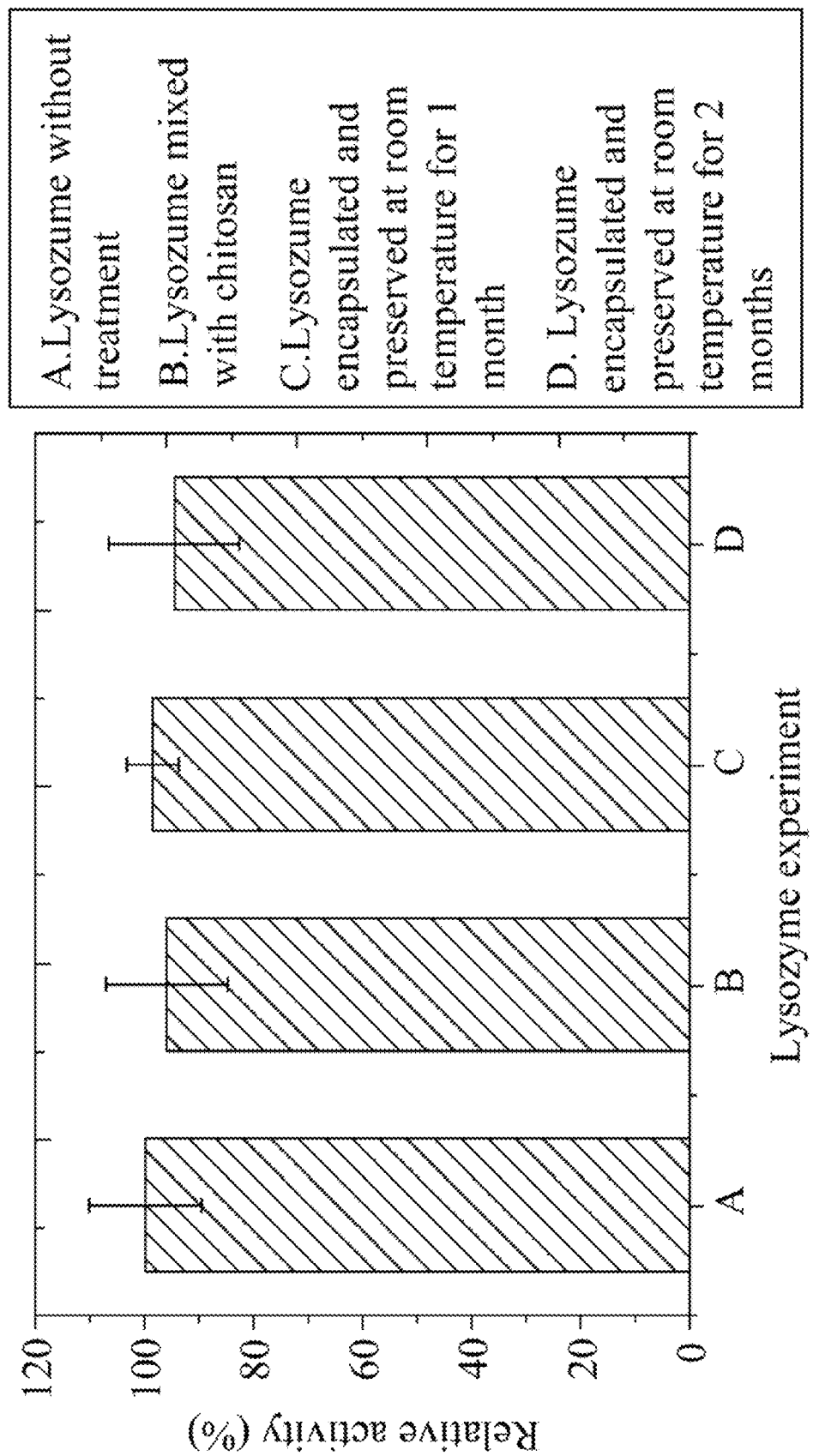
FIG. 8 is a testing result for biological activity of lysozyme according to an embodiment of the present invention.

In the embodiment, 5.0 mg of lysozyme is taken as a drug and encapsulated into the carriers of the transdermal patch. The carriers are tested with its enzymatic activity after respectively preserving at room temperature for one month and two months. Its tested result is shown in FIG. 8. It should be noted that enzymatic activities of the lysozyme that is not encapsulated, the lysozyme mixed with chitosan solution, the lysozyme that has been preserved and encapsulated at room temperature for one month, and the lysozyme that has been encapsulated and preserved at room temperature for two months do not have obvious difference.

In another aspect of the embodiment, sprague dawley (SD) rats having four to six weeks of age are divided into three groups. Immune response is induced at zero day and fourteenth days by respectively encapsulating 1 mg of ovalbumin in the embeddable micro-needle patch for transdermal drug delivery, injecting saline in muscles, and injecting 1 mg of ovalbumin solution in muscles so as to produce correspondingly IgG antibodies, and blood is drawn from venous sinus under collarbones of the rats at zero day, seventh day, fourteenth day and twenty-first day. The drawn blood is detected by ELISA (enzyme-linked immunosorbent assay) to obtain 450 nm absorbance such that the contents of IgG antibodies antibody induced by ovalbumin in blood serum are determined.

Figure 9:
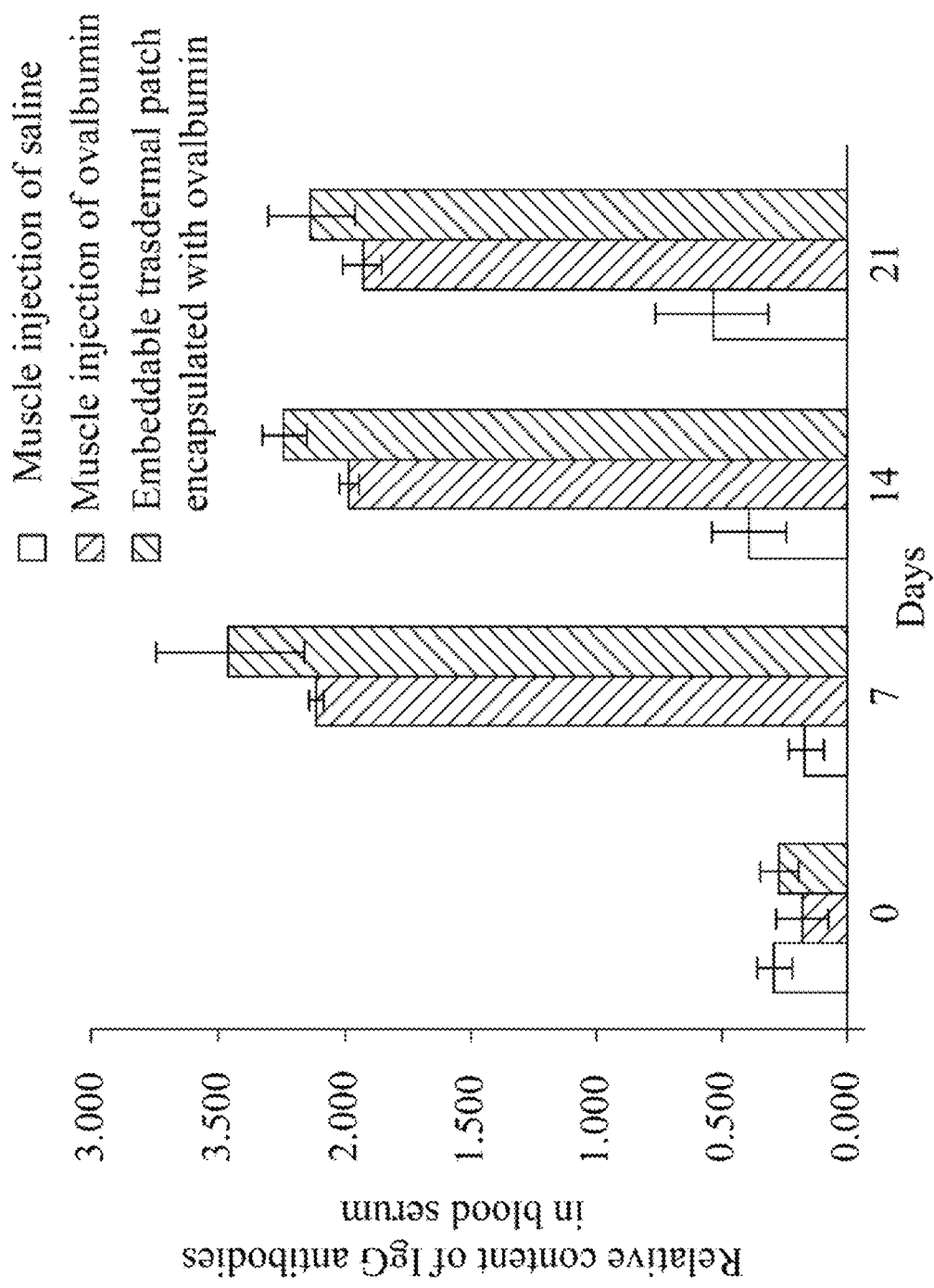
FIG. 9 is an immunity testing result.

The result is shown in FIG. 9 for an immunity test result. By comparing with the control group of injecting saline in muscles, the expression of inducing IgG antibodies in blood serum can be discovered at seventh day regardless of the groups that use the embeddable micro-needle patch for transdermal drug delivery encapsulated with ovalbumin or injects ovalbumin in muscles. It shows that it still has activity after injecting the drugs encapsulated in the embeddable micro-needle patch for transdermal drug delivery according to the present invention into organism bodies. Moreover, IgG antibodies content in blood serum induced by the embeddable micro-needle patch for transdermal drug delivery is obviously higher than the groups of conventional muscle injection at seventh day and fourteenth day. The foregoing result shows that the embeddable micro-needle patch for transdermal drug delivery according to the present invention can deliver antigens and induce stronger immune response than conventional muscle injection through transdermal drug delivery.

With the foregoing results, the drugs encapsulated in the transdermal drug delivery according to the present invention can have activity and stability under the preservation at room temperature or while injecting into organism bodies.

It should be noted that the embodiment takes antigens as an example for the drugs encapsulated in the carriers. However, the drugs are not restricted and further include the hydrophilic drugs or macromolecular drugs having a molecular weight greater than 500 Da, which are both difficult to penetrate through skin cuticle, such as DNA (deoxyribonucleic acid), macromolecular protein, vaccine, peptide, bacteria or chemical synthetic drug.

Next, the subsequent paragraphs will provide an example of sustained release of the drugs through the transdermal patch according to the present invention.

In the embodiment, the embeddable micro-needle patch for transdermal drug delivery containing chitosan carriers encapsulated with ovalbumin, chitosan carriers having trehalose encapsulated with ovalbumin, and chitosan carriers having trehalose encapsulated with FITC-dextran having fluorescent protein, penetrates through epidermis of the porcine cadaver skin for five minutes. Next, the carriers are separated from the supporting shafts to embed into epidermis of the porcine cadaver skin. Epidermis of the porcine cadaver skin that has been penetrated is placed in a transdermal absorbing device fully filled with 5 ml of phosphate buffered saline solution (PBS, pH=~6). Afterward 200 µl solution within the transdermal absorbing device is taken out everyday, and the ELISA is utilized to test the drug content within the solution. Since trehalose has higher thermal stability and wider pH value stability scope, trehalose molecules having multiple hydroxyl group can replace water molecules mutually interacted with active substances through hydrogen bonds during the drying step of preparing carriers. Thus, the structural completeness of the drugs or vaccines encapsulated in the carriers can be retained so as to steady the drugs in the carriers. However, it can, but not limited to, also be applied to different kinds of substances having the foregoing stability.

Figure 10:
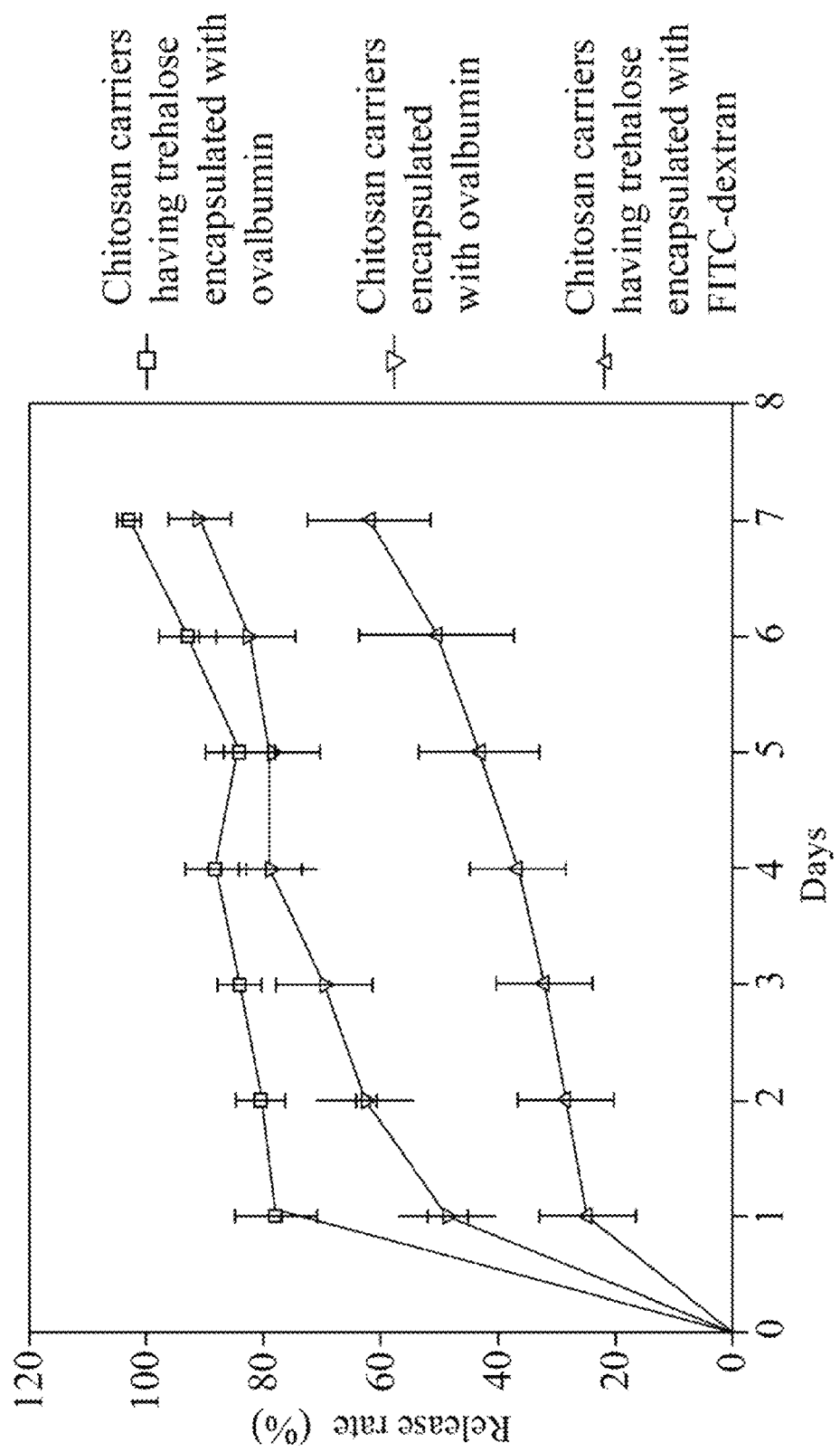
FIG. 10 is a result for in vitro drug release profile evaluated in a Franz diffusion cell via different carriers.

The result is shown in FIG. 10 for the drug release profiles of three kinds of carriers into the porcine cadaver skin, wherein in the groups of chitosan carriers encapsulated with ovalbumin or chitosan carriers encapsulated with ovalbumin containing trehalose, it can be found that about 80% to 100% drugs can be released at seventh day. In another word, the drugs can be continuously released for seven days. In addition, if chitosan with larger molecular weight is taken as the carrier to deliver the same sizes' drugs, its effect of sustained release will be more remarkable than chitosan carriers with smaller molecular weight although it is not shown in the figure. Moreover, in FIG. 10, the chitosan carriers encapsulated with FITC-dextran, which contains trehalose, merely release about 40% to 60% drugs in seventh day. Therefore, it can expect that the drugs could be continuously released about fourteen days.

Under a condition of the same carrier, if the molecular weight of encapsulated drugs is larger, drug release period would be longer. In addition, under the situation of encapsulating the same drugs, if the molecular weight of the carrier is larger, its molecular chains is easily wound the drugs such that the drugs are not easily released from the carriers, thus extending the drug release period. Based on these, the transdermal patch according to the present invention can control drug release rat by regulating the molecular weight of the carrier materials or the drugs.

The carriers of the transdermal patch according to the present invention are formed by biodegradable polymeric materials. It can be naturally degraded in organism bodies to release the drugs encapsulated therein and may not cause metabolic burden of the user and does not have the problem of medical waste (discarded needles) as well. In addition, the transdermal patch according to the present invention is to separate the carrier from the supporting substrates and embed the carriers into skin. Its operation is simple and does not need to apply the transdermal patch on skin for long time to cause uncomfortable of the user. Further, the transdermal patch according to the present invention could control the drug release rate by regulating its carrier materials, thereby achieving the sustained release of the drugs.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. An embeddable micro-needle patch for transdermal drug delivery, comprising:
    a supporting substrate, one surface of the supporting substrate containing a plurality of protruded insertable solid supporting shafts, configured to be inserted into a skin while applying the embeddable micro-needle patch to the skin, wherein a height of the plurality of protruded insertable solid supporting shafts is within a range from 600 μm to 900 μm, and a base width of the plurality of protruded insertable solid supporting shafts is within a range from 200 μm to 400 μm, and the height and the width of the protruded insertable solid supporting shafts contribute to insertion into the skin, wherein a material of the protruded insertable solid supporting shafts is a polymeric material;
    a biodegradable carrier, configured to be fully inserted into the skin while applying the embeddable micro-needle patch to the skin, formed by a biodegradable polymeric material and disposed on the plurality of protruded insertable solid supporting shafts, wherein a height of the biodegradable carrier is within a range from 400 μm to 800 μm, and a base width of the biodegradable carrier is within a range from 200 μm to 400 μm, and the height and the width of the biodegradable carrier contribute to insertion into the skin, wherein a surface area of each of the plurality of protruded insertable solid supporting shafts facing the biodegradable carrier is smaller than a surface area of the biodegradable carrier facing each of the plurality of protruded insertable solid supporting shafts, wherein an adhesive coated on the plurality of protruded insertable solid supporting shafts contains polyethylene glycol (PEG), polyethylene oxide (PEO), polyvinylpyrrolidone (PVP), gamma-polyglutamic acid (γ-PGA), gelatin, xanthan gum and derivatives thereof; and
    a drug encapsulated in the biodegradable carrier, wherein the drug is uniformly mixed with the biodegradable carrier, wherein the adhesive is coated on the protruded insertable solid supporting shafts to adhere to the biodegradable carrier, and the adhesive is configured to be dissolved within the skin after the embeddable micro-needle patch is applied on the skin for a predetermined time, such that the biodegradable carrier is embedded into the skin by separating from the plurality of protruded insertable solid supporting shafts, and the biodegradable carrier is swollen and then is degraded to release the drug encapsulated in the biodegradable carrier into the skin at a speed of 1% loaded drug per day to 99% loaded drug per day.

2. The embeddable micro-needle patch for transdermal drug delivery of claim 1, wherein the predetermined time is 3 minutes to one hour.

3. The embeddable micro-needle patch for transdermal drug delivery of claim 1, wherein a polymeric material of the supporting substrate contains poly-lactic acid (PLA), polyglycolic acid (PGA), poly-lactide-co-glycolide (PLGA), polydioxanone (PDS) or derivatives thereof.

4. The embeddable micro-needle patch for transdermal drug delivery of claim 1, wherein a shape of the biodegradable carrier comprises a micro-needle, a pyramid, a cone or any shape capable of enabling the biodegradable carrier penetrating though the skin.

5. The embeddable micro-needle patch for transdermal drug delivery of claim 1, wherein a depth for the biodegradable carrier penetrating through the skin is 20 μm to 1000 μm.

6. The embeddable micro-needle patch for transdermal drug delivery of claim 1, wherein the drug contains a macromolecular drug in which a molecular weight is greater than 500 Da or a hydrophilic drug.

7. The embeddable micro-needle patch for transdermal drug delivery of claim 1, wherein the drug contains deoxyribonucleic acid (DNA), protein, vaccine, peptide, bacteria or chemical synthetic drugs.

8. The embeddable micro-needle patch for transdermal drug delivery of claim 1, wherein the biodegradable polymeric material contains chitosan, chitin, silk, carboxymethyl cellulose (CMC), chondroitin, collagen, gelatin, crosslinked material thereof, derivatives thereof, or polysaccharide derivatives.

9. A method for manufacturing the embeddable micro-needle patch for transdermal drug delivery as recited in claim 1, the method comprising:
    mold-filling a biodegradable polymer gel containing the drug to obtain a plurality of the biodegradable carriers, wherein the drug is uniformly mixed with the biodegradable carrier; and adhering the plurality of the protruded insertable solid supporting shafts on the surface of the supporting substrate to the plurality of biodegradable carriers to form the embeddable micro-needle patch for transdermal drug delivery.

10. The method of claim 9, wherein the step of mold-filling the biodegradable polymer gel containing the drug further comprises placing the biodegradable polymer gel containing the drug on a surface of a mold to perform centrifugation such that the biodegradable polymer gel containing the drug is injected into cavities of the mold.

11. The method of claim 10, wherein the step of mold-filling the biodegradable polymer gel containing the drug further comprises performing the biodegradable polymer gel containing the drug, which is injected into the cavities of the mold, with a centrifugal force such that the biodegradable polymer gel containing the drug is concentrated at bottoms of the cavities of the mold.

12. The method of claim 10, wherein the step of mold-filling the biodegradable polymer gel containing the drug further comprises concentrating the biodegradable polymer gel containing the drug, which is injected into the cavities of the mold, at bottoms of the cavities contained by the mold through a pressing tool.

13. The method claim 10, wherein the cavity of the mold is a micro-needle column, a pyramid column or a cone column shape.

14. The method of claim 9, wherein the plurality of the protruded insertable supporting shafts are adhered to the plurality of the biodegradable carriers by coating the adhesive.

* * * * *